United States Patent [19]

Hendriks

[11] 4,209,591
[45] Jun. 24, 1980

[54] ENZYMATIC CONVERSION PROCESS

[75] Inventor: Petrus F. A. M. Hendriks, Geleen, Netherlands

[73] Assignee: Stamicarbon, B.V., Geleen, Netherlands

[21] Appl. No.: 930,860

[22] Filed: Aug. 3, 1978

[30] Foreign Application Priority Data

Aug. 19, 1977 [NL] Netherlands .................. 7709179

[51] Int. Cl.² .............................................. C12M 1/40
[52] U.S. Cl. ..................................... 435/288; 435/813
[58] Field of Search .................. 195/2, 108, 127, 115, 195/116, 139, DIG. 11; 422/140, 142, 191, 195; 210/17, 150, 151; 435/288, 813

[56] References Cited

U.S. PATENT DOCUMENTS

| | | | |
|---|---|---|---|
| 3,079,222 | 2/1963 | Reeve | 422/142 |
| 3,525,590 | 8/1970 | Botton et al. | 422/142 |
| 3,928,143 | 12/1975 | Coughlin | 195/115 |
| 4,032,407 | 6/1977 | Scott et al. | 195/116 X |
| 4,048,018 | 9/1977 | Coughlin et al. | 195/115 |
| 4,088,571 | 5/1978 | Helgesson | 210/150 X |
| 4,138,290 | 2/1979 | McMullen et al. | 195/DIG. 11 |

OTHER PUBLICATIONS

Lilly et al., "Immobilized Enzyme Reactors", Methods of Enzymology Academic Press Publishers, 1976, vol. XLIV, pp. 717–725.

*Primary Examiner*—R. B. Penland
*Attorney, Agent, or Firm*—Cushman, Darby & Cushman

[57] ABSTRACT

Chemical enzymatic conversions are conducted by contacting an aqueous solution of the substrate with a granular immobilized enzyme, the substrate solution being passed through several series-connected, separate fluidized beds of the granular enzyme, while the enzyme particles are passed from one fluidized bed to the next countercurrently and against the direction of flow of the substrate solution. Multi-compartment reactor columns are also disclosed.

5 Claims, 2 Drawing Figures

ENZYMATIC CONVERSION PROCESS

BACKGROUND OF THE INVENTION

The invention relates to a process for effecting a chemical conversion by contacting a substrate in the liquid phase with an immobilized enzyme.

It is known to chemically convert an organic or inorganic compound into one or more other compounds by putting a solution of the substrate into contact with an immobilized enzyme or mixture of enzymes. Chemical conversion here comprises any change of the molecular structure of an organic or inorganic compound, such as those caused by hydrolysis, oxidation, reduction, isomerization, or racemization. Enzymes can be immobilized by physical or chemical binding to an organic or inorganic material or by crosslinking the enzyme or cell material with enzymatic activity, optionally in the presence of a filler.

On a technical scale, glucose is thus converted into a mixture of glucose and fructose by means of immobilized glucose isomerase, and N-acetyl L-amino acids are deacylated by means of immobilized amino acylase. In this process it is customary to pass the solution of the substrate through a fixed or fluidized bed of immobilized enzyme particles. Owing to the loss of enzymatic activity, the content of the reactor must be renewed at intervals. For reasons of process economy, it is customary in nearly all cases to replace the immobilized enzyme preparation as soon as its activity has dropped to a given value, usually 20 to 25% of the original activity, both in a discontinuous process in a single reactor and in a semicontinuous process in a single series-connected reactors. A drwaback of this process is that the residual activity of the enzyme preparations is not utilized.

The use of a fixed bed of enzyme particles has the additional drawback that the pressure build-up of such a bed is great owing to coagulation or swelling of the enzyme particles. It is also possible that channels are formed in the fixed enzyme bed. It is an object of the present invention to provide a process in which the enzymatic activity of the enzyme preparation can be utilized fully or almost fully. Another object is to make the conversion of the substrate as complete as possible.

DETAILED DESCRIPTION OF THE INVENTION

According to the present invention, the chemical conversion of a compound is effected by putting an aqueous solution of the substrate into contact with a granular immobilized enzyme so that the substrate solution is passed through a number of series-connected, separate fluidized beds of granular immobilized enzyme, while the enzyme particles are passed discontinuously from a fluidized bed to an adjacent fluidized bed countercurrently against the direction of flow of the substrate solution.

Some advantages of the process according to the present invention are that it can be effected continuously in a direct manner that the enzyme preparation can be used until the activity has dropped to only a small percentage of the original activity, that the pressure differences over the column are small, and that the degree of conversion of the substrate can be very high, especially when dilute substrate solutions are used. A further advantage is that the costs of construction and operation of the column used according to the present invention are lower than for known processes even when the process is conducted until 20 or 25% of the activity remains, as in the known processes mentioned above.

The process of the present invention is conveniently conducted in a column reactor filled with liquid, the column being divided by horizontal partitions, which are pervious to the substrate solution, into several superposed compartments, each such compartment containing a fluidized bed of granular immobilized enzyme. The reactor is provided with means for the transport of enzyme from one compartment to the next against the direction of flow of the substrate solution. A column reactor of this type is compact and can be constructed and operated in a simple manner.

According to one process aspect of the present invention, a granular immobilized enzyme is used with a specific gravity lower than that of the substrate solution. In this case the substrate solution is fed to the top of the column and discharged at the bottom, while the fresh immobilized enzyme is fed to the lowest compartment of the column. An immobilized enzyme for use in this embodiment can be obtained by immobilizing a free enzyme by cross-linking in the absence of fillers, or by using a filler or support of low specific gravity in the immobilization. In this case the fluidization is brought about by the tendency of the enzyme particles to rise in the contacted liquid and the opposite downward force of the flow of substrate solution.

It is preferred to use a granular immobilized enzyme with a specific gravity greater than that of the substrate solution. In this case the substrate solution is passed upwards through the column and fresh enzyme is fed to the top compartment of the reactor. From the top compartment of the reactor it is passed successively through the lower series of compartments, in each of which the enzyme loses part of its activity. A more detailed discussion of this embodiment follows. This embodiment is to be preferred as it is compatible with the technological know-how of fluid-beds and allows greater variation in the types of granular immobilized enzyme to be used.

The process according to the present invention has some marked advantages in addition to the utilization of the enzyme and the almost complete conversion of the substrate as mentioned above. Thus, the column can be operated at a constant feed rate of the substrate solution and, unlike the reaction in a fixed bed, it is not necessary to make up for the loss in activity of the enzyme preparation by decreasing the amount of substrate supplied to the column. In conversions in which a gaseous reactant is used, such as air in oxidative conversions, the air may be fed to the bottom of the column. A number of sieve trays or grids are used causing the gas to be redistributed over and over again, and no channels or large gas bubbles are formed.

The reaction conditions can be accurately and conveniently controlled by adding some reactants or auxiliary substances to one or more of the compartments. For instance, when a base or acid is released in the conversion, the best pH can still be maintained by adding an acid, base or buffer to the column as required in one or several places.

Substrate characteristics can be matched with enzyme activity requirements most conveniently according to this process. Thus, if the substrate itself has an activating effect, this effect is utilized fully, as the substrate concentration is highest in those parts of the reactor where the enzymatic activity of the enzyme preparation has fallen most. Conversely, inhibition, if any, by the conversion products or byproducts causes comparatively less interference, as the concentration of such inhibitors is highest in those places where the activity of the enzyme preparations is also highest. The process furthermore has the advantages inherent in the use of a fluidized bed, such as better temperature control, proper transfer of matter, and reduced susceptibility to contamination, such as infections and bacterial growth.

The process of the present invention is particularly suitable for effecting reactions that take place fully or partly in the Michaelis range. In this range, the conversion rate depends not only on the enzymatic activity, but also on the substrate concentration. The substrate concentration is low in the upper part of the column, but the activity of the immobilized enzyme preparation is high, so that a satisfactory conversion rate can still be reached. As a result, the process of this invention can be used for conversions with an enzyme with a low Michaelis constant and for conversions that have to proceed as completely as possible. Some examples are the treatment of waste water from which materials such as phenol are removed by means of phenol oxidase, or urea is removed by means of urease; the treatment of optically active substrates, such as the preferential hydrolysis of L-phenyl-glycine amide in the presence of D-phenyl-glycine amide by means of amino-acid amide deamidase; and the conversion of penicillin G into 6-amino-penicillanic acid by means of penicillin amidase. The advantage of the invention clearly appears from the fact that the urea content of a waste-water flow can be reduced to below 10 p.p.m. by the present process.

The process according to the present invention furthermore has the advantage that the apparatus required is simpler to construct and to operate. In the known processes at most three or five reactors could be arranged in series. In such system the reactor that has operated longest may be shut down at regular intervals, emptied and filled with fresh enzyme and started again as the last of the series. Each time the substrate solution is connected to another reactor. A larger number of reactors is hardly feasible because of the cost and the pressure drop across the system. In the invention ten or more fluidized beds can be used in series without any problem, so that the enzyme can be more efficiently used and a more complete conversion of the substrate is possible.

The transport of enzyme particles from one compartment to the next lower compartment may be effected in various ways, illustrative embodiments of which will now be described. As a first embodiment, overflow pipes may be installed that pass through the partition between two compartments and connect the two compartments. The overflow pipe ends at the top side at some distance over the partition. The distance between the end of the overflow pipe and the partition is the maximum height of the fluidized bed. When fresh enzyme particles are fed to the top compartment, the height of the fluidized bed rises and the surplus flows through the overflow pipe to the next lower compartment, where it causes the transport of enzyme particles to the next lower compartment. Enzyme particles that have completely lost their activity or nearly all of their activity are discharged from the lowest compartment.

In this first embodiment, the partition between the compartments permits passage of the substrate solution only, under normal operating conditions. The partition used may be a sieve plate or guaze. The overflow pipes may also be arranged to extend to the outside of the column with outlet opening in the column wall. The lower side of the overflow pipe ends in the fluidized bed and preferably tapers towards the end. The pipes are staggered with respect to each other. A column reactor of this type is simple to construct and to operate. A minor drawback is that the flow rate of the substrate solution must be controlled properly, otherwise the fluidized bed might expand too strongly at peak values of the flow rate, so that enzyme products would flow prematurely to the lower compartment.

Enzyme particle movement and transfer may also be controlled by providing each compartment with a pipe through which enzyme particles cam be discharged to the next lower compartment by a pump, optionally by way of a buffer vessel. The procedure may be such that the enzyme is first discharged from the lowest compartment. Next, the enzyme is pumped from the last compartment in the form of a slurry which is transferred to the lowest compartment, optionally by way of a buffer vessel. In this embodiment the flow rate of the substrate solution is much less critical. The larger investment in equipment pipes and a pump is usually offset by greater reliability in operation.

The transport of immobilized enzyme particles can also be controlled by partitioning the compartments using sieve trays or other functionally equivalent members that do not allow enzyme product to pass at a liquid flow rate of over a given predetermined threshhold value, but do allow enzyme product to pass to the next lower zone at a flow rate between the minimum fluidization rate and that threshhold value. Such a partition may consist of a plate with a number of adjacent truncated conical recesses that are open at the lower end. In this case the liquid feed is reduced periodically, so that the enzyme particles sink to the lower zone and exhausted enzyme particles are discharged from the bottom of the column while an equal amount of fresh enzyme particles is supplied to the top of the column.

It will be understood that further embodiments for the transport of the enzyme particles are possible. Use might also be made of trays provided with valves, either located flush with the surface or mounted in short overflow tubes. If the above-described methods, the first two are preferred because of their simplicity and reliability.

The reaction conditions are preferably selected such that the reactivity of the enzyme discharged from the reactor is at most 10 to 15% of the initial activity, and, preferably, less than 5% of the starting activity. Under certain conditions it may be advantageous, as described below hereinafter, to have one or more compartments even contain fully deactivated enzyme. Other reaction conditions will depend on the nature of the liquid phase substrate being treated and the particular enzymatic conversion or conversions to be accomplished. In some cases it may be economically sound to carry out the reaction under such conditions that the residual activity of the discarded enzyme is somewhat higher, for instance between 15% and 20% of the initial activity.

The typical reactor will include at least three separate compartments and, preferably, at least five. For practical reasons, one will preferably use a reactor from 5 to 20 compartments. The compartments, or the fluidized beds contained in them, need not all have the same volume.

The average retention time of the granular immobilized enzyme in the reactor to a large extent depends on the type of enzyme, the substrate and the reaction conditions. The average retention time will generally range between about a week and several months. The average retention time of the substrate in the reactor depends on a number of factors, some of which include the type of substrate, the type of enzyme, the substrate concentration and the desired degree of conversion. The average retention time of the substrate generally ranges between 0.5 and 120 minutes, in most cases between 5 and 60 minutes.

The substrate to be converted is fed into the reactor in the form of a solution, preferably aqueous, that may optionally contain other reactants as may be required, such as pH regulators, activators, agents for binding interfering impurities, and inert compounds. Emulsions may also be used. If so desired, the substrate solution may been pre-treated, such as by degassing, sterilization, treatment with activated carbon, or similar customary procedures. The substrate solution first contacts the enzyme product that has fully or largely lost its enzymatic activity.

The substrate solution may contain impurities, for instance, heavy metals, that deactivate the enzyme by physical or chemical combination with the enzyme. In this case it is advantageous to use a first zone containing a sufficient number of enzyme particles such that the impurities are substantially or completely to the enzyme particles that are then discharged from the system.

The concentration of the substrate in the solution may vary within wide limits, the only requirement being that the solution can still cause proper fluidization of the enzyme particles as described above. If the conversion step is part of a synthesis system, the substrate concentration may be as much as 50% by weight or more, but in most cases it will be between about 5 and about 30% by weight, which also depends on the solubility of the substrate. However, if the object of the conversion is to remove impurities, the concentration is usually much lower, in the order of about 0.01 to about 1% by weight. The rate at which the substrate solution is passed through the column primarily depends on the fluidization behavior of the enzyme particles and the reactor design. The optimum flow rate can be determined from theoretical calculations or tests by a skilled operator. In most cases, a flow rate of between about 0.5 and about 20 cm/sec may be used.

The granular enzyme products used in the process of the present invention are prepared in various ways. Preference is generally given to products of a granular organic or inorganic support to which the enzyme, cells, or cell parts containing enzyme have been bound either directly or by means of a coupling agent. Products obtained by cross-linking enzymes or cell materials, optionally in the presence of a filler, followed by shaping or any other process yielding fluidizable particles are also used. Various other enzyme products may be used, for instance, products obtained by precipitation of enzymes or a cell material with a flocculant, followed by molding, or products obtained by incorporation of enzymes or cell material in an organic polymer matrix, or binding enzymes or cell material to a polymer, which may be cross-linked. Particularly suitable supports or fillers include glass, sand, silica, carbon, alumina, zirconium oxide, titanium oxide and metals such as nickel. If desired, the support or filler may have been pretreated to effect a better bond. Specific coupling agent may be selected from poly-functional compounds such a glutaric aldehyde, silanes, polyisocyanates, azides, polycarboxylic acids and anhydrides thereof.

The overall dimensions, shape and specific gravity of the particles of the enzyme product are chosen such that these particles are readily fluidized and do not only slightly separate into various fractions under operating conditions. As is generally known and reported, there exists a relationship between the diameter and shape of the particles, their specific gravity, and the flow rate to be used in the fluidized bed in the liquid phase. When possible, the dimensions and shape of the particles are selected such that the bed expansion is about 2 at a flow rate of about 4 to about 5 cm/sec. The specific gravity of the particles depends largely on the amount and the nature of the filler.

Many of the granular enzyme products useful in the present invention are themselves described in the art, including their manner of preparation, physical size and properties as well as their biological specificity for the substrate which is to be treated. The physical aspects of these granules such as specific weight and size are selected so as to be functional to best advantage in the process of the present invention by maintaining a substantially or completely fluidized condition in the substrate liquid under operational conditions.

The particular type of enzyme used in the process of the present invention depends upon the type of enzymatic conversion desired provided, of course, the enzyme has sufficient activity once immobilized to carry out the required conversion. The choice of enzyme type need not be limited and as representative classes or types of enzymes belonging to the classes of the hydrolases, the oxidases, the isomerases and the transferases may be used. Some specific examples include amino-acid acylase, amino-acid amidase, peptidase, urease, phenol oxidase, inulase, lactase, asparaginase, fumarase, glucose-oxidase, penicillin amidase, hydantoinase, trypsin, papain, chymotrypsin, aminopeptidase. It is also possible to use a mixture of enzymes instead of only one enzyme. One may also feed an additional amount of granular immobilized enzyme into the column at a position between the inlet and outlet of the enzyme. This additional enzyme may be an enzyme type other than the one fed to the top of the column.

The temperature at which the conversion reaction is conducted is selected within the range defined by the melting point of the substrate solution and the temperature at which the enzyme is deactivated, which range is generally between 0° and 80° C. and preferably between about 20° and about 60° C. It will be apparent that the temperature chosen depends primarily on the enzyme used.

The pressure at which the conversion is effected is of little importance in most cases the process is conveniently conducted at approximately atmospheric pressure. If gaseous reactants are used in the conversion, or gaseous products are formed, it may be advantageous to use a higher reaction pressure in order to maintain the gaseous compounds dissolved in the aqueous phase. As an example, in the decomposition of urea with immobilized urease, an absolute pressure of between 5 and 10 bar may be used in order to keep ammonia and carbon dioxide in solution. The reaction may also be effected at a lower pressure so that gaseous reactants or products are present. In this case the column must be provided with a gas-liquid separator connected to a gas outlet.

The pH at which the conversion is effected is selected such that the optimum enzymatic activity of the immobilized enzyme is obtained which, or course, is related to the particular enzyme employed. In most cases this is a pH of between 6.0 and 8.0. However, there are certain enzymes which may used at a much lower pH such as between 3.5 and 5, or on the other hand, at higher pH such as between 8.5 and 10.5. The skilled operator will easily determined the appropriate pH required for optimum activity of the enzyme or enzyme system used.

BRIEF DESCRIPTION OF THE DRAWINGS

The present invention, in both its process and apparatus aspects will now be elucidated with reference to the appended drawings, in which.

DETAILED DESCRIPTION OF THE DRAWINGS

Figure 1:
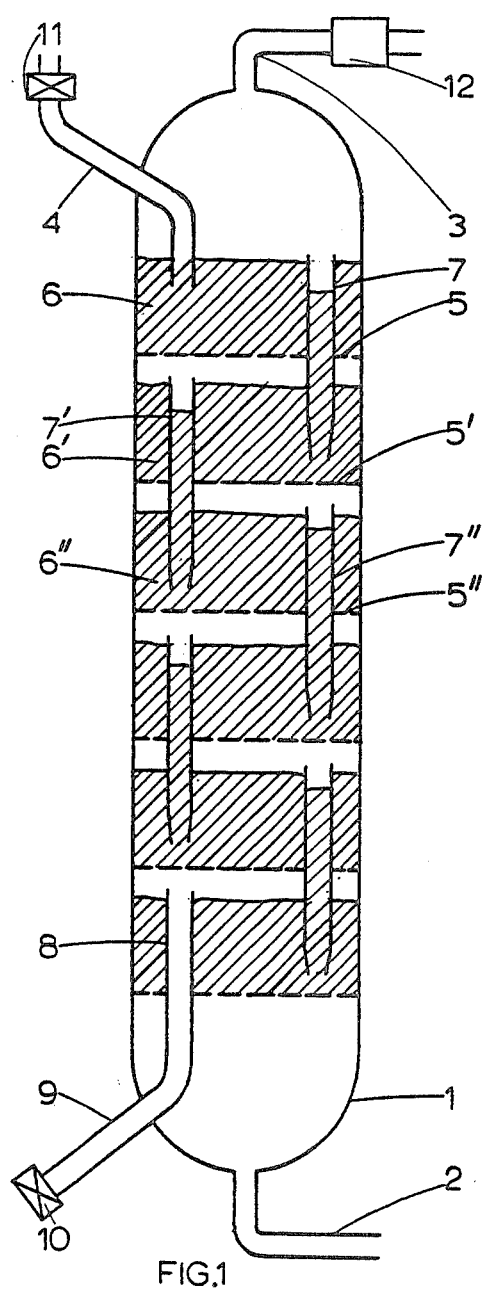
FIG. 1 is a cross-section view of an interconnected compartment counterflow fluidized-type reactor.

In FIG. 1 a column reactor 1 is provided at the bottom with a supply tube 2 for substrate solution and at the top with an outlet 3 for the discharge of the converted product solution. The column is also provided at the top with an enzyme supply tube 4 for immobilized granular enzyme in dry form or in the form of an aqueous slurry.

A number of horizontal sieve trays 5, 5', 5" divide the column into a corresponding number of compartments containing fluidized beds 6, 6' and 6" of enzyme particles. The compartments communicate through overflow pipes 7, 7' and 7".

Overflow pipe 8 from the lowest compartment becomes a discharge pipe 9 for the exhausted enzyme, which is connected through valve 10 with a settling vessel or other means for separating and discharging the enzyme.

Under operating conditions the column is completely filled with liquid; the substrate solution is passed through the column from the bottom to the top. The level of the fluidised beds is preferably maintained somewhat below the top of the overflow pipes. Just before fresh particulate immobilised enzyme is fed to the column the level of the fluidised beds may be brought up to the top of the overflow pipes by increasing the liquid flow. Intermittently an amount of fresh enzyme in the form of a slurry is forced in the column through valve 11 and conduit 4. This causes a transport of enzyme downwards through the column and discharge of enzyme through overflow 8, pipe 9 and valve 10. The outlet may be connected to a gas-liquid separator 12. If the presence of enzyme particles in the product solution is not tolerated, outlet 3 may also be connected to a filter in order to remove any fine particles that may have been entrained by the liquid flow.

Figure 2:
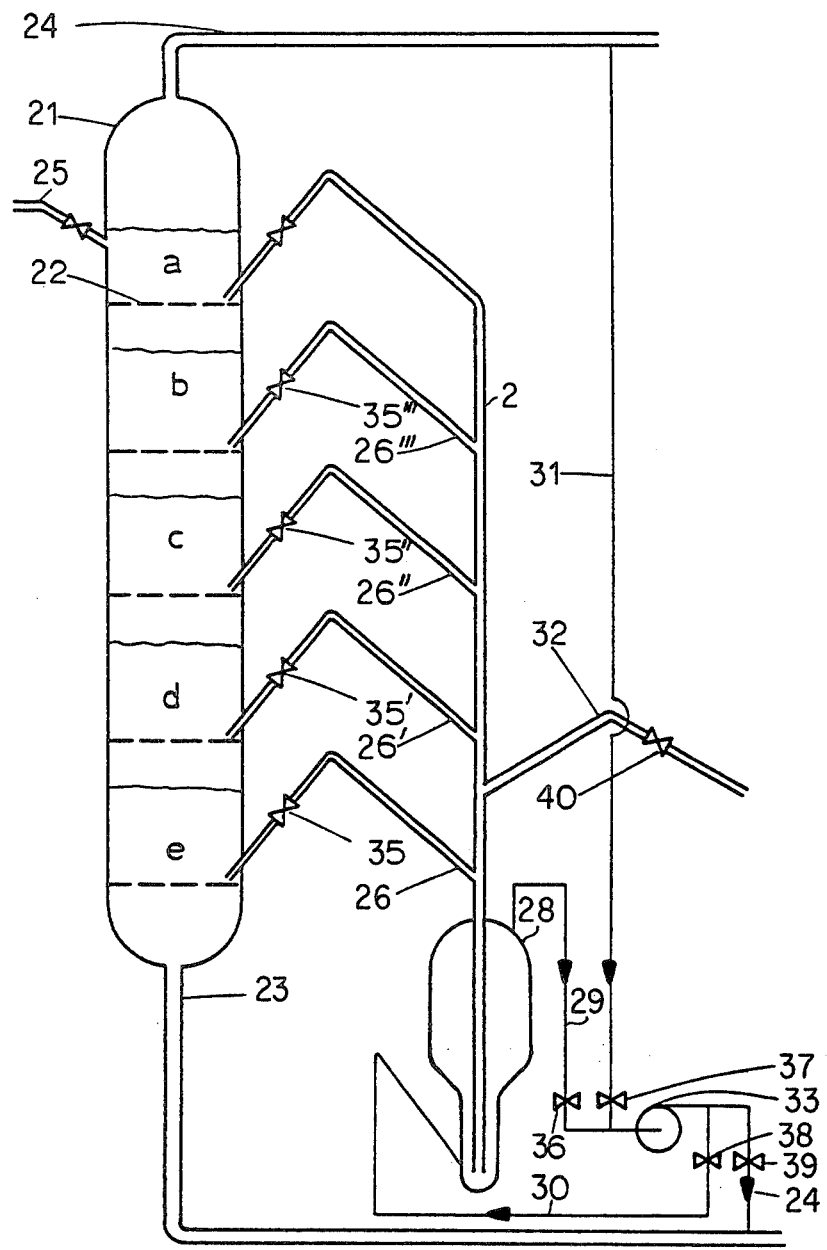
FIG. 2 is a part schematic, part-cross-sectional view of a multi-compartment reactor including a common transfer pipe system, and associated fluid transfer equipment according to the present invention.

Another embodiment of the invention is shown in FIG. 2 in which the column reactor 21 is provided with a number of sieve trays 22 that divide the reactor into a corresponding number of compartments a, b, c, d and e. The reactor is also fitted with a supply tube 23 for the substrate solution, an outlet 24 for the process liquor containing the substrate, and a feed tube 25 for fresh granular enzyme. Each compartment is provided with a pipe 26 connected to a common pipe 27, which in turn, terminates in a storage tank 28. Storage tank 28 is provided, at the top, with a liquid discharge pipe 29 that is connected to the suction side of a pump 33. Tank 28 is also provided, at the restricted side, with a liquid feed pipe 30 that is connected to the delivery side of pump pipe 33. Pipe 31 connects pipe 24 to the suction side of pump 23 and pipe 24 connects the delivery side of pump 33 to pipe 23. Valves 35, 35' and 35" are provided in pipes 26, 26' and 26". Pipe 29 is provided with valve 36, pipe 30 with valve 38, pipe 31 with valve 37, and pipe 34 with valve 39. Pipe 27 is connected to a discharge pipe 32 with valve 40 for discharging the exhausted enzyme.

Under normal operating conditions the entire system is filled with liquid and all valves are closed. The substrate solution flows upwardly through the column and keep the enzyme in each of the compartments a through 3 in a fluidized state. In the enzyme transfer mode the enzyme in compartment e is emptied first. While the supply of substrate solution is maintained unchanged, pipe 33 is started and valves 35, 36 and 39 are opened. As a result, the enzyme particles are passed in the fluidized state or as a slurry from compartment e through conduits 26 and 27 into tank 28.

The liquid flow thus transferred is so small that conditions in the other compartments hardly change. Common pipe 27 terminates at the bottom of tank 28 which is provided with a restricted portion which serves to promote discharge of the particles under conditions of permanent fluidization. As the liquid flow pumped through pipes 29 and 34 is small, the enzyme particles collect in tank 28 in the fluidized state while pipes 29 and 34 and pump 33 remain free of solids. When all the enzyme has been removed from compartment e, valves 35, 36 and 39 are closed and valves 37, 38 and 40 are opened. The enzyme particles are then pushed from tank 28 and discharged through pipes 27 and 32. In the next step, the contents of compartment d are transported to the tank in the manner described above and then transported to compartment e. Likewise, the contents of the other compartments are transferred to the next lower compartment. Finally a charge of fresh enzyme particles is fed to the top compartment. If so desired, the various pipes, valves and the intermediate storage tank may be provided with connections to a rinsing system for rinsing the equipment with clean water.

It will be noted that the pipes 26, 26', 26" and 26''' extend into the fluid beds at an angle of for instance between 30° and 80° to the horizontal. The purpose of this positioning is so the interior of these pipes stays free of solid particles when valve 35 is closed. The restricted lower portion of the intermediate storage tank is important to ensure that all enzyme particles can be removed from the tank again with the aid of the delivery pipe. The transport medium used for emptying the various compartments is substrate solution, which is returned to the column. The medium used to fill the various compartments is the substrate-free effluent. In this manner, contamination is avoided. For convenience of illustration, a reactor having only five compartments is shown in the figure. It will be understood that a greater number of compartments, such as 10 or more, will be used in a practice with this type of reactor.

The partitions may consist of sieve trays provided with apertures having a diameter greater than the size of the particulate material. If the liquid flow decreases or is interrupted. The enzyme could in such case fall down the length of the column and gather at the bottom. In order to avoid this other partitions, e.g. bubble-cap trays, may be used or obstructions may be provided.

Very suitable are beams of triangular cross-section mounted above each row of apertures, such that the base of the beam which is wider than the diameter of the apertures is at a small distance above the surface of the tray. The substrate solution can flow upwards through the apertures and the space between the tray and the base of the beam. If the liquid flow decreases, the particulate material gathers and settles in the through-like space between adjacent beams. When the liquid flow again reaches the fluidisation velocity the particles move upwards and are fluidised.

The invention will be further described by means of the following working Examples. Unless otherwise indicated all parts and percentages are by weight.

EXAMPLE 1

150 grams of sand (screening fraction 175–250 $\mu$m) are added with stirring and under nitrogen conditions 2150 ml of fermentation liquid obtained by culturing *Bacillus pasteuri* in a 5-liter vessel. Then over a period of 10 minutes, 350 ml of 0.1% solution of the flocculant Praestol 44 K were added, after which stirring was continued for another 15 minutes. The precipitate was filtered and washed three times with 300 ml of water containing 1 mmol/l of mercapto-ethanol. The solid mass consisting of sand and cellular material was dried at 55° C. and a pressure of 16 kPa for 2.5 hours. 151.2 grams of dry solid product were obtained.

In the next stage, 149 g of the solid mass were stirred in a mixture of 175 ml of acetone and 69 ml of an aqueous solution of mercapto-ethanol (1 mmol/l) while nitrogen was passed through. Over a period of 2 minutes 6.5 ml of a 20% aqueous solution of glutaric dialdehyde at a pH of 7.0 were added to this suspension at room temperature, after which stirring was continued for another 20 minutes. The solid mass was then filtered, washed four times with 150 ml of aqueous mercapto-ethanol soluton (1 mmol/l), dried for 2 hours at 50° C. under reduced pressure (16 kPa) and ground into particles.

The urease activity of the resulting granular product was 28.5 units per gram of solids. The activity was determined according to known procedures by adding 2.0 g of solids to 50 ml of a 2% urea solution in a 0.1 molar Sorensen glycine buffer with a pH of 9.2 at a temperature of 40° C. The amount of $CO_2$ formed at 40° C. in 15 minutes was determined calorimetrically. The activity was expressed in units, being the amount of substrate, in micromoles, that is converted per weight unit of enzyme in one minute.

When the sand consists of the screening fraction in excess of 250 $\mu$m granular immobilized enzyme is obtained which has an activity of 26.6 units per gram of solids.

These granular enzyme preparations are used in the apparatus described in the following Example.

EXAMPLE 2

Flow Rate And Bed Expansion Study

A reactor for conducting the process according to the present invention consisted of a tube with an internal diameter of 114 mm and a length of 2200 mm, in which six trays were fitted 300 mm apart. Each tray was provided with 42 apertures 2 mm in diameter and was perforated by an overflow pipe 11 mm in internal diameter extending 100 mm above the tray and 280 mm below the tray. The lower end of each overflow pipe was tapered to a diameter of 5 mm. The lower end of the tube communicated with a collecting tank fitted wirh stop-cock for exhausted enzyme and a liquid feed pipe. The tube was provided at the top with a liquid outlet. The apparatus can be used at flow rates of up to 0.05 m/s. At a flow rate of 0.01 m/s the bed expansion is about 2 if particles having an irregular shape with a diameter of 176–380 $\mu$m and a specific gravity weight of 2650 kg/m$^3$ are used. When particles of 516–840 $\mu$m in diameter are used a bed expansion of 2 is reached at a flow rate of 0.025 m/s.

EXAMPLE 3

Treatment of Urea-Containing Waste Liquid

Waste-water containing 1.0 wt. % of uera can be treated by the process according to the present invention in a reactor formed by a column 9.45 m length and 1.20 m in internal diameter that is divided, by means of horizontal sieve trays, into ten compartments each with a height of 0.67 m and containing 453 kg of immobilized urease granules in the fluidized state. The sieve trays are designed as described in Example 2 and are provided with overflow pipes reaching to 0.46 m above the trays. The top of the column is provided with a liquid inlet and the bottom is provided with a liquid outlet. A feed pipe for fresh immobilized enzyme empties itself in the top compartment and the overflow pipe of the lowest compartment is connected to a discharge line.

A suitable enzyme preparation is obtained by immobilising cell material containing urease, obtained from a culture of *Bacillus pasteuri*, with sands as a filler in a weight ratio of 1 to 5. A fluidisable particulate material is thus obtained with an average particle size of 300 to 700 $\mu$m, a specific gravity of 1780 kg/m$^3$, an initial activity of 300 units/g and a half-life of 1000 hours. The fluidisation velocity is from 0.0035 to 0.025 m/s. The amount of waste-water is about 30.9 m$^3$/hr, at a pH of about 9, a temperature of 35° C. and a pressure of 300 kPa. Each compartment contains 453 kg of enzyme preparation and under normal conditions the bed height is 0.45 m. The amount of urea left in the treated wastewater and the residual activity of the enzyme which is discarded both depend on the amount of fresh enzyme. If 72 kg of the fresh particulate immobilised enzyme are introduced once every 48 hours, the treated solution will contain about 10 ppm of urea and the activity of the enzyme discarded will be about 9% of the initial activity. If 100 kg of enzyme are introduced once every 48 hours the treated solution will contain about 2 ppm of urea and the activity of the enzyme discarded will be about 16.5% of the initial activity.

What is claimed is:

1. A continuous process for the enzymatic chemical conversion of a substrate solution by contacting the substrate solution with granular immobilized enzyme in an expanded or fluidized state, said process comprising:
    (a) passing a substrate solution continuously in an upward direction through a single column reactor which is divided by horizontal partitions pervious to the substrate solution into at least three compartments, each compartment containing a fluidized bed of granular immobilized enzyme having a specific gravity greater than that of the substrate solution, said partitions being substantially impervious to the granular enzyme
    (b) periodically passing said granular immobilized enzyme in a downward direction from each compartment to the next lower compartment, feeding fresh enzyme to the upper compartment and discharging spent enzyme from the lowest compartment, and (c) continuously removing the solution containing converted substrate from the top of the column.

2. The process according to claim 1 wherein the granular immobilized enzyme has a specific weight in excess of about 1.0 and is passed downwardly while the substrate solution passes through said enzyme in an upward direction.

3. The process according to claim 1 wherein said discharged spent enzyme has less than about 15% of its original enzymatic activity.

4. The process according to claim 3 wherein said discharged spent enzyme has less than about 5% of that original enzymatic activity.

5. The process according to claim 1 wherein said column reactor contains from 5 to 20 of said compartments.

* * * * *